United States Patent [19]

Spatz

[11] Patent Number: 4,654,346
[45] Date of Patent: Mar. 31, 1987

[54] FUNGICIDAL N,N-DISUBSTITUTED-HETEROCYCLIC CARBOXAMIDES

[75] Inventor: David M. Spatz, Fairfax, Calif.

[73] Assignee: Chevron Research Company, San Francisco, Calif.

[21] Appl. No.: 690,784

[22] Filed: Jan. 11, 1985

Related U.S. Application Data

[62] Division of Ser. No. 439,243, Nov. 4, 1982, Pat. No. 4,504,484.

[51] Int. Cl.$^4$ .................. A61K 31/495; C07D 239/02
[52] U.S. Cl. .................................... 514/255; 514/248; 514/256; 514/357; 514/400; 544/238; 544/335; 544/336; 544/406; 546/313; 546/316; 548/378; 548/342
[58] Field of Search ............... 544/238, 335, 336, 406; 514/255, 248, 256

[56] References Cited

U.S. PATENT DOCUMENTS 3,869,456  3/1975  Taylor et al. .................. 260/251
3,991,071  11/1976  Brookes et al. ................ 548/341
4,080,462  3/1978  Brookes et al. ................ 424/273 R
4,504,484  3/1985  Spatz .............................. 544/335

FOREIGN PATENT DOCUMENTS 1570034  12/1969  Fed. Rep. of Germany .

OTHER PUBLICATIONS

Brookes et al, Chem. Abst. 82-156306h.
Brookes et al, Chem. Abst. 89-163572q.
Chemical Abstracts, vol. 73, 55265c (1970).
Kozlik et al, Chem. Abst. 79-53327z.
Beilstein Handbuch Der Organicchen Chemie (1931) pp. 129, 162, 1773, 1733.
Beilstein Handbuch Der Organischen Chemie (1923), pp. 251, 252, 256,257, 258, 264,265, 292, 293, 342, 343, 344.
Aldrich Fine Chemicals (1986), pp. 433, 516, 1092, 1093, 1315, 1288, 1319.

Primary Examiner—Donald G. Daus
Assistant Examiner—Cecilia Shen
Attorney, Agent, or Firm—S. R. LaPaglia; T. G. DeJonghe; S. L. Biggs

[57] ABSTRACT

The substituted heteroaryl compounds of this invention are good fungicides. In particular, they possess especially good activity against Bean Powdery Mildew.

43 Claims, No Drawings

FUNGICIDAL N,N-DISUBSTITUTED-HETEROCYCLIC CARBOXAMIDES

This is a division of application Ser. No. 439,243, filed Nov. 4, 1982, now U.S. Pat. No. 4,504,484.

BACKGROUND OF THE INVENTION

This invention is drawn to novel fungicides.

With the world more dependent for food on an ever decreasing amount of cultivated farmland, it is increasingly important to develop effective fungicides which protect crops from fungicidal destruction.

Kozlik et al, in CA 79:53327Z, disclosed 1-carbamolyimidazoles as insecticidal.

Brookes et al, in U.S. Pat. Nos. 4,080,462 and 3,991,071, disclosed 1-(N,N-disubstituted carbamoyl and thiocarbamoyl)-imidazoles as fungicidal.

SUMMARY OF THE INVENTION

The compounds of the present invention are represented by the formula:

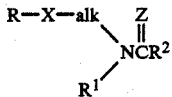

wherein R is phenyl, or phenyl substituted with 1 to 3 substituents independently selected from fluoro, chloro, bromo, iodo, nitro, lower alkyl, lower alkoxy, lower alkyl or lower alkoxy substituted with 1 to 3 of the same or different halogens; $R^1$ is lower alkyl, or —$CH_2Y$ wherein Y is lower alkenyl, lower alkenyl substituted with 1 to 3 of the same or different halogens, lower alkynyl, lower alkynyl substituted with 1 to 3 of the same or different halogens, lower alkoxyalkyl, lower alkoxy, lower alkylthioalkyl, lower thioalkyl, lower hydroxyalkyl, lower haloalkyl, or halogen; $R^2$ is a 6-member heterocyclic ring containing 1 to 2 nitrogen atoms and the remainder carbon atoms, a 6-member heterocyclic ring containing 1 to 2 nitrogen atoms and the remainder carbon atoms with the ring substituted with 1 to 2 independent lower alkyl groups, a 5-member heterocyclic ring containing 1 to 2 nitrogen atoms and the remainder carbon atoms, or a 5-member heterocyclic ring containing 1 to 2 nitrogen atoms and the remainder carbon atoms with the ring substituted with 1 to 2 independent lower alkyl groups, with the proviso that a nitrogen of the 5- or 6-member heterocyclic ring is not bonded to the

group; Z is sulfur, or oxygen; X is sulfur, oxygen, or represents a direct linkage between R and alk; and alk is a branched- or straight-chain alkylene group of 1 to 10 carbons with the proviso that the chain length is no longer than 5 carbons.

Among other factors, the present invention is based on my finding that the compounds of this invention are effective fungicides. In particular, some of the compounds of this invention possess good activity against Bean Powdery Mildew.

In part due to their superior fungicidal activity, preferred R groups include the trihalophenyl and dihalophenyl groups. Particularly preferred R groups are 2,4,6-trihalophenyl and 2,6-dihalophenyl.

Preferred halogens include bromo and chloro.

Preferred $R^1$ groups include, for instance, lower hydroxyalkyl, lower alkyl and lower alkenyl groups. A particularly preferred $R^1$ group is lower alkyl. Especially preferred $R^1$ groups are ethyl or n-propyl.

Preferred $R^2$ groups include, for instance, 3-pyridyl, 5-pyrimidyl, 2-pyrazyl and 5-(1-methylimidazoyl).

Preferred alk groups include, for instance, methylene, ethylene, propylene, 1-methylethylene, and the like. Especially preferred are compounds where alk is ethylene.

DEFINITIONS

As used herein, the following terms have the following meanings, unless expressly stated to the contrary.

The term "alkenyl" refers to unsaturated alkyl groups having a double bond [e.g., $CH_3CH=CH(CH_2)_2—$,] and includes both straight- and branched-chain alkenyl groups.

"Lower alkenyl" groups refer to alkenyl groups having from 2 through 6 carbon atoms. Typical lower alkenyl groups include, for example, ethylene, but-3-enyl, hex-4-enyl, 2-methylpent-4-enyl, and the like.

The term "alkynyl" refers to unsaturated alkyl groups having a triple bond [e.g., $CH_3\equiv C(CH_2)_2—$] and includes both straight- and branched-chain alkynyl groups.

The term "lower alkynyl" refers to alkynyl groups having from 2 through 6 carbon atoms and includes, for example, but-3-ynyl, hex-4-ynyl, 3-methylpent-4-ynyl, and the like.

The term "alkyl" refers to both straight- and branched-chain alkyl groups. Generally, such alkyl groups contain from 1 through 12 carbon atoms.

The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "halo" or "halogen atom" refers to the groups fluoro, chloro, bromo and iodo.

The term "alkoxy" refers to the group R'O— wherein R' is alkyl.

The term "lower alkoxy" refers to the alkoxy groups having from 1 through 6 carbon atoms and includes, for example, methoxy, ethoxy, t-butoxy, hexoxy, and the like.

The term "lower alkoxyalkyl" refers to groups having the formula R"OR'"— wherein R" and R'" are independently lower alkyl. Typical lower alkoxyalkyl groups include, for instance, methoxymethyl, methoxypropyl, isopropoxybutyl, hexoxyhexyl, and the like.

The term "lower hydroxyalkyl" refers to the group HOR"— wherein R" is lower alkyl. Such groups include, for example, hydroxymethyl, hydroxyethyl, hydroxyhexyl, and the like.

The term "thioalkyl" refers to the group having the formula R'S— wherein R' is alkyl.

The term "lower thioalkyl" refers to such alkylthio groups wherein the alkyl group is lower alkyl. Typical lower alkyl groups include, for example, methylthio, ethylthio, t-butylthio, and the like.

The term "lower alkylthioalkyl" refers to the group R"SR'"— wherein R" and R'" are independently lower alkyl. Typical lower alkylthioalkyl groups include, for instance, methylthiomethyl (e.g., CH₃SCH₂—), ethylthiomethyl (e.g., CH₃CH₂SCH₂—), and the like.

The term "haloalkyl" refers to alkyl groups having one or more halo substituents. Typical haloalkyl groups include, for example, trifluoromethyl, dichloromethyl, bromochloromethyl, 1,2-dibromoethyl, 3-iodopropyl, chloromethyl, and the like.

The term "a 6-member heterocyclic ring containing 1 to 2 nitrogens" refers to the groups pyridyl, pyridazinyl, pyrimidyl, pyrazinyl, and the like.

The term "a 5-member heterocyclic ring containing 1 to 2 nitrogens" refers to the groups imidazolyl, pyrrolyl, pyrazolyl, and the like.

The term "alk" refers to straight- and branched-chain alkylene groups of 1 to 10 carbons and includes, for instance, ethylene, propylene, 2-methylpropylene (e.g.,

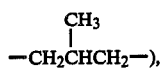

3-methylpentylene

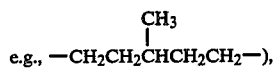

and the like.

The term "ethanolamine" refers to the group HOCH₂CH₂NH₂.

The term "N-(3-pyridylcarbonyl) ethanolamine" refers to the group:

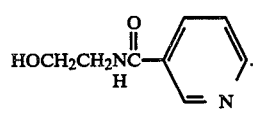

The term "N-(3-pyridylcarbonyl) ethanolamine 2,4,6-trichlorophenylether" refers to the group:

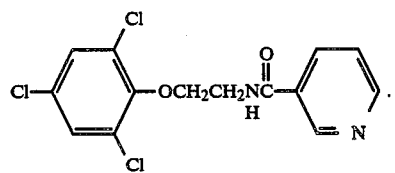

The term "N-(n-propyl), N-(3-pyridylcarbonyl) ethanolamine 2,4,6-trichlorophenylether" refers to the group:

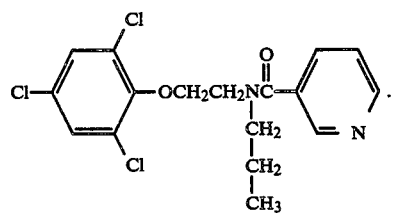

The term "2-aminoethanethiol" refers to the group HSCH₂CH₂NH₂.

The term "N-(3-pyridylcarbonyl), N-(n-propyl) 2-aminoethanethiol" refers to the group:

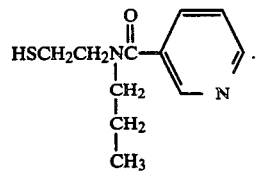

The term "N-(n-propyl), N-(3-pyridylcarbonyl) 2-aminoethanethiol 4-t-butylphenylthioether" refers to the group:

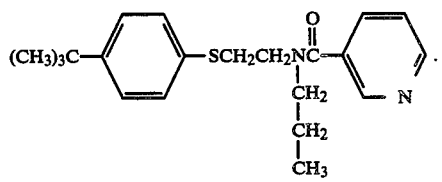

The term "ethylenediamine" refers to the group H₂NCH₂CH₂NH₂.

The term "nicotine amide" refers to the group:

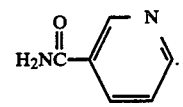

The term "pyrazinamide" refers to the group:

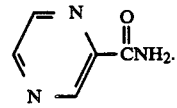

DETAILED DESCRIPTION OF THE INVENTION

The compounds of the present invention wherein X is oxygen or sulfur and alk is not an α-branched-chain alkylene group are conveniently prepared according to the following synthetic scheme:

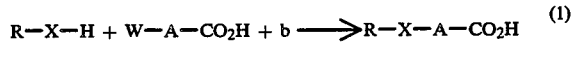

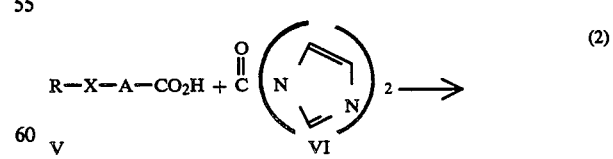

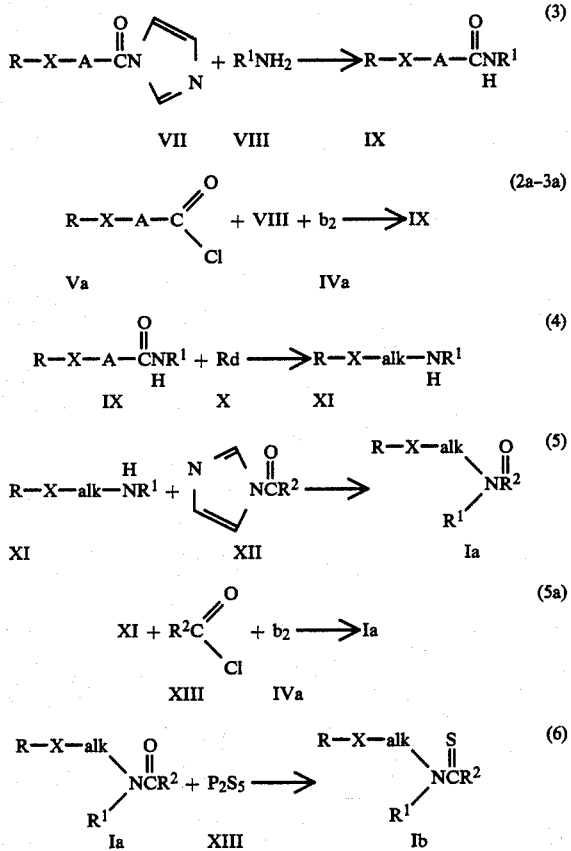

wherein R, $R^1$, $R^2$ and alk are as defined above; W is a halogen, b is a base, $b_2$ is an acid scavenger (a base), Rd is a reducing agent and A is an alkylene group 1 carbon shorter in length than the resulting alk group.

Reaction (1) is conducted by adding approximately 2 equivalents of a base, IV, to II. The reaction is done in the liquid phase employing an organic solvent such as ethanol, methanol, and the like, or alternatively water. Preferably, the base employed is an inorganic base. Suitable inorganic bases include, for instance, sodium hydride, sodium methoxide, metallic sodium, and the like. After addition of IV, an approximately equimolar amount of III is added to the system. Reaction pressure is not critical and for convenience, the reaction is generally conducted at atmospheric pressure. The reaction is generally conducted at from 0° C. to 100° C., although preferably at from 40° C. to 70° C., and is generally complete from within 1 to 48 hours. The resulting intermediate, V, is isolated by conventional procedures such as extraction, filtration, chromatography, distillation, or alternatively, used in Reaction (2) without purification and/or isolation.

Reaction (2) is conducted by adding an essentially equimolar amount of carbonyldiimidazole, VI, to V. The reaction is conducted in the liquid phase using an inert anhydrous organic solvent such as chloroform, methylene chloride, dimethoxyethane, toluene, and the like. Reaction pressure is not critical and for convenience, the reaction is generally conducted at atmospheric pressure. The reaction is generally conducted at from 0° C. to 100° C., although preferably at room temperature, and is generally complete from within 1 to 24 hours. The resulting carboxylic acid imidazolide, VII, may be isolated by conventional procedures such as extraction, filtration, chromatography, distillation, and the like. Alternatively and preferably, the resulting intermediate is not isolated from the reaction solution, but is used directly in Reaction (3).

Reaction (3) is conducted by adding an essentially equimolar amount of the appropriate primary amine, VIII, to VII. The reaction is conducted in the liquid phase using an inert anhydrous organic solvent such as chloroform, methylene chloride, dimethoxyethane, toluene, and the like. Preferably, the reaction solution is the same as was employed in Reaction (2) with the appropriate amine, VIII, merely added to the system after completion of Reaction (2). Reaction pressure is not critical and for convenience, the reaction is generally conducted at atmospheric pressure. The reaction is generally conducted at from 0° C. to 100° C., although preferably at room temperature, and is generally complete from within 1 to 24 hours. The resulting amide, IX, is isolated by conventional procedures such as extraction, filtration, chromatography, distillation, or alternatively, used in Reaction (4) without purification and/or isolation.

Alternatively, IX may be prepared according to Reaction (2a-3a) by adding a solution of the acid chloride corresponding to V to a solution of VIII. The acid chloride Va is prepared from the acid V by techniques known to the art, such as treatment with thionyl chloride. The reaction is conducted in the presence of $b_2$ (IVa), an acid scavenger such as triethylamine, pyridine, an alkylamine, sodium carbonate, or the like. The reaction is conducted in the liquid phase using an inert organic solvent such as methylene chloride, chloroform, dioxane, toluene, and the like. The reaction is carried out at a temperature of about $-50°$ C. to about 100° C., preferably from about 0° C. to about 25° C. After the addition is complete, the reaction mixture is allowed to return to room temperature. The reaction is generally complete within about 0 to about 48 hours after the addition is complete. The resulting amide IX is isolated by conventional procedures such as extraction, filtration, chromatography, distillation, or alternatively used in Reaction (4) without further purification or isolation.

Reaction (4) is a conventional reduction of the amide to the amine.

In preparing compounds of this invention, the carbonyl of the amide is reduced to the methylene group; the reaction is conveniently conducted by adding an essentially equimolar amount of a reducing agent, Rd, to IX. The reaction is conducted in the liquid phase employing an inert anhydrous organic solvent such as toluene, benzene, and the like. Suitable reducing agents include, for instance, lithium aluminum hydride, borane, borane methyl sulfide, and the like. Preferably, due to the ease in handling the reagent, borane methyl sulfide is employed as the reducing agent. However, when $R^1$ is a group susceptible to an undesired reaction with borane or borane methyl sulfide (such as allyl, propargyl, and the like), the preferred reducing agent is lithium aluminum hydride. Reaction pressure is not critical and for convenience, the reaction is conducted at atmospheric pressure. The reaction is generally conducted at from 0° C. to 110° C., although preferably at from 30° C. to 70° C., and is generally complete from within 1 to 24 hours. The resulting amine, XI, is isolated by conventional procedures such as extraction, filtration, chromatography, distillation, or alternatively, used in Reaction (5) without purification and/or isolation.

Reaction (5) is conducted by first preparing reagent XII. XII is prepared by adding an essentially equimolar amount of carbonyldiimidazole to the appropriate acid, $R^2CO_2H$ wherein $R^2$ is as defined above. The reaction is conducted in the liquid phase using an inert anhydrous organic solvent such as chloroform, methylene chloride, dimethoxyethane, toluene, and the like. Reaction pressure is not critical and for convenience, the reaction is generally conducted at atmospheric pressure. The reaction is generally conducted at from 0° C. to 100° C., although preferably at room temperature, and is generally complete from within 1 to 24 hours. The resulting reagent, XII, may be isolated by conventional procedures such as extraction, filtration, chromatography, distillation, and the like. Alternatively and preferably, the reagent is not isolated from the reaction solution but an essentially equimolar amount of the amine, XI, is added to the system. Reaction pressure for this reaction is not critical and for convenience, the reaction is generally conducted at atmospheric pressure. After addition of XI, the reaction is generally conducted at room temperature and is generally complete from within 1 to 24 hours. The product, Ia, is then isolated by conventional procedures such as extraction, filtration, chromatography, distillation, or alternatively, used in Reaction (6) without purification and/or isolation.

Alternatively, product Ia may be prepared by Reaction (5a) using the acid chloride XIII corresponding to $R^2CO_2H$. Acid chloride XIII may be conveniently prepared by combining approximately equimolar amounts of $R^2CO_2H$ and thionyl chloride. The reaction is conducted in the liquid phase using an inert organic solvent such as methylene chloride, toluene, chloroform, and the like. It is preferred to conduct the reaction in the presence of a catalytic amount of dimethylformamide. The reaction mixture is heated to reflux and refluxed for about 0 to about 24 hours. The mixture is stirred until gas evolution ceases. After the temperature of the mixture returns to room temperature, XIII may be used in Reaction (5a) without purification or isolation. Since XIII is susceptible to hydrolysis, minimal handling of it is preferred.

Reaction (5a) is conducted by combining XIII, with XI and IVa. The reaction is conducted in the liquid phase using an inert organic solvent such as methylene chloride, chloroform, toluene and the like. Suitable acid scavengers, $b_2$ (IVa), include bases such as triethylamine, pyridine, an alkylamine, sodium carbonate, and the like. The reaction is carried out at a temperature of about −25° C. to about 100° C., preferably from about 0° C. to about 25° C., and may be conveniently carried out at room temperature. The reaction is generally complete within about 0 to about 24 hours. Product Ia is then isolated by conventional procedures such as extraction, filtration, chromatography, distillation, or alternatively, used in Reaction (6) without purification and/or isolation.

Reaction (6) is conducted by adding an essentially equimolar amount of phosphorus pentasulfide, XIII, to I. The reaction is conducted in the liquid phase using an inert anhydrous organic solvent such as toluene, tetrahydrofuran, and the like. Preferably, the system is exposed to microwave radiation in order to facilitate the dispersion of phosphorus pentasulfide into solution. Reaction pressure is not critical and for convenience, the reaction is generally conducted at atmospheric pressure. The reaction is generally conducted at from 15° C. to 100° C., although preferably it is conducted at the ambient temperature and is generally complete from within 1 to 48 hours. The product is then isolated by conventional procedures such as extraction, filtration, chromatography, distillation, and the like.

The compounds of this invention wherein X is oxygen or sulfur and alk is an α-branched-chain alkylene group are conveniently prepared according to the following synthetic scheme:

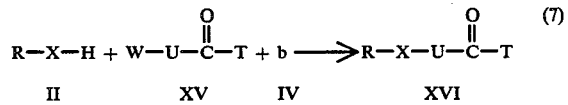

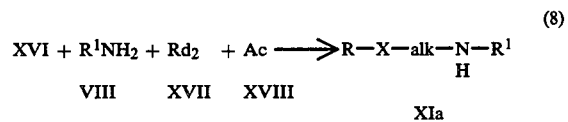

wherein R and $R^1$ and b are as defined above; W is a halogen; Ac is an acid; U is an alkylene group and T is an alkyl group such that the sum of the number of carbon atoms in U and T is one carbon less than the number in alk; and $Rd_2$ is a reducing agent.

Reaction (7) is conducted by adding approximately equimolar amounts of II and XV to IV in solvent. The reaction is done in the liquid phase employing an organic solvent such as ethanol, methanol, and the like. Preferably, the base employed is an inorganic base. Suitable inorganic bases include, for instance, sodium hydride, sodium methoxide, metallic sodium, and the like. Reaction pressure is not critical and for convenience, the reaction is generally conducted at atmospheric pressure. The reaction is generally conducted at from about 25° C. to about 100° C., although preferably at from about 60° C. to about 78° C., and is generally complete within about 2 to about 48 hours. The resulting intermediate, XV is isolated by conventional procedures such as extraction, filtration, chromatography, or distillation.

Reaction (8) is conducted by adding an excess of VIII and XVII to a stirred mixture of XV in solvent. The reaction is conducted in the liquid phase employing an inert anhydrous organic solvent such as methanol, ethanol, acetonitrile, and the like. Suitable reducing agents include those which are relatively mild and selective and include for instance, sodium cyanoborohydride, sodium borohydride, and the like. The preferred reducing agent is sodium cyanoborohydride. After the addition is complete, the system is acidified to a pH of about 5 to 6 using acid XVIII, preferably a non-aqueous acid such as hydrogen chloride gas. The reaction is generally conducted at from about 0° C. to about 50° C., and for convenience, it may be conducted at ambient temperature. The reaction is generally complete within about 1 to about 24 hours. The resulting amine XIa may be isolated by conventional procedures such as extraction, filtration, chromatography, and the like, or used without purification and/or isolation is Reaction (5).

The amine XIa is then converted to the compounds of this invention as outlined in Reactions (5) and (6).

The compounds of this invention wherein X represents a direct linkage between alk and R are conveniently prepared by starting with the appropriate reagent V and following Reactions (2) through (6).

Alternatively, these compounds may be prepared from the appropriate 3-phenyl, 3-substituted phenyl, or α- and/or β-substituted cinnamic acid as the starting material for Reaction (2). Reaction (3) is then conducted as above. However, in Reaction (4), an additional equivalent of boron methyl sulfide is required in order to saturate the vinylic group. After Reaction (4), the synthesis is accomplished through Reactions (5) and (6) as described above.

UTILITY

The compounds of the invention are effective in controlling fungal infections. Some of the compounds of this invention are particularly effective in controlling powdery mildew fungal infections caused by the organism *Erysiphe polygoni*. Some of the compounds of this invention are also useful for controlling leaf blights caused by organisms such as *Phytophthora infestans conidia, Alternaria solani conidia,* and *Septoria apii*. Some of the compounds of this invention are also useful for controlling fungal infections caused by *Uromyces phaseoli tipica, Plasmopara viticola,* and *Piricularia oryzae*. However, some fungicidal compounds of this invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

Compounds which were prepared in accordance with Examples 1 through 22 below are found in Tables I to IV.

EXAMPLES

Example 1

Preparation of 2,4,6-trichlorophenoxyacetic acid 2,4,6-trichlorophenol, 100.7 gm, was added to 250 ml of ethanol. 228.6 ml of a 25% solution of sodium methoxide (2 equivalents) in methanol was then added to the system. The system was stirred at room temperature for approximately 1 hour. Afterwards, 69.5 gm of bromoacetic acid was added an the system then heated to reflux. After 18 hours, an additional equivalent of sodium methoxide in methanol (114.3 ml) was added as well as 34.7 gm of bromoacetic acid. The system was continued at reflux for 12 hours. The reaction was then stopped and the solvent removed by stripping. The resulting solid was washed with water and then with ether. Concentrated HCl was next added to the solid precipitate and the system was left standing for 12 hours. Afterwards, the product was filtered, washed with water and air dried. Toluene was then added to the product. The toluene was removed by stripping and any remaining water was azeotroped off with the toluene. 74.4 gm of 2,4,6-trichlorophenoxyacetic acid was recovered.

Example 2

Preparation of N-(n-propyl)-2,4,6-trichlorophenoxyacetamide (a) 2,4,6-trichlorophenoxyacetic acid, 47.5 gm, was added to 300 ml of methylene chloride along with 30.3 gm of carbonyldiimidazole. The system was stirred overnight to give the carboxylic acid imidazolide.

(b) 15.4 ml of n-propylamine was then added to the system. The system was then stirred at room temperature for an additional 20 hours. The reaction was stopped and the organic solution was washed first with a dilute HCl solution, then with a sodium bicarbonate solution and then with water. The methylene chloride was removed by stripping to give the N-(n-propyl)-2,4,6-trichlorophenoxyacetamide.

Example 2a

Preparation of N-(n-propyl)-2,4,6-trichlorophenoxyacetamide

A solution of 2625 gm (9.62 moles) 2,4,6-trichlorophenoxyacetic acid chloride in methylene chloride (total solution weight 5403 gm) was added to a solution of 1251 gm (21.17 moles) n-propylamine in 7.6 methylene chloride in a 22-liter flask over a period of 2 hours. During the addition, the temperature of the system was maintained at about 5° C. to 7° C. using a dry ice/isopropyl alcohol bath. During the addition, some white solids precipitated. After the addition was complete, the cooling bath was removed allowing the temperature of the system to rise to 10° C. over 25 minutes. The system temperature was then raised to 23° C. over 10 minutes by use of a warm water bath. Sample NMR and IR spectra indicate the reaction was complete. After removal of the warming bath, the methylene chloride solution was washed 3 times with 4 water. The aqueous layer and organic layers were separated and the organic phase was dried over 150 gm magnesium sulfate. The organic solution was stripped until the weight reached about 3 kg. While the system was still in the hot water bath, 3.5 hexane was added, giving a clear solution. The system was then cooled to 20° C., giving a very thick slurry of crystals. The crystals were filtered and washed with 2 hexane. Air drying gave 2102 gm.

The mother liquor and hexane washings were stripped to give 450 gm of a brown oil which solidified upon cooling. Recrystallization from hexane (about 900 ml), followed by filtering the crystals, washing the crystals with hexane (about 500 ml), and air drying gave an additional 342 gm of the product.

Example 3

Preparation of N-(n-propyl) ethanolamine 2,4,6-trichlorophenylether

N-(n-propyl)-2,4,6-trichlorophenoxyacetamide, 44.0 gm, was added to 250 ml of toluene. 28 ml of borane methyl sulfide [BH$_3$.(CH$_3$)$_2$S] (2 equivalents) was then slowly added to the system. The system was heated at approximately 60° C. for 15 hours at which time reaction completion was checked by IR spectroscopy. 200 ml of methanol was then slowly added to the system. After addition of the methanol, the system was acidified by bubbling in HCl gas. Afterwards, the system was refluxed for 1 hour. The solvent was then removed by stripping. The resulting oil was dissolved in methanol which was then stripped. The oil was next dissolved in methylene chloride. The organic solution was washed with a sodium hydroxide solution and then with water. The methylene chloride was removed by stripping to give 36.3 gm of the N-(n-propyl) ethanolamine 2,4,6-trichlorophenylether, as a yellow oil.

Example 4

Preparation of N-(n-propyl), N-(2-pyrazinylcarbonyl) ethanolamine 2,4,6-trichlorophenylether (a) 2-pyrazine carboxylic acid, 2.5 gm, was added to 10 ml of methylene chloride. 3.2 gm of carbonyldiimidazole was added to the system. The system was stirred at room temperature for 3 hours to give the 2-pyrazine carboxylic acid imidazolide.

(b) N-(n-propyl) ethanolamine 2,4,6-trichlorophenylether, 5.6 gm, was then added to the system. The system was stirred at room temperature for 16 hours. The reaction was then stopped and the methylene chloride solution was washed with a sodium bicarbonate solution, then with a dilute solution of hydrochloric acid and finally with water. The methylene chloride solution was dried over magnesium sulfate and the methylene chloride removed by stripping to give 6.2 gm of the N-(n-propyl), N-(2-pyrazinylcarbonyl) ethanolamine 2,4,6-trichlorophenylether as a yellow oil, listed as Compound No. 3 in Table I.

Example 4a

Preparation of N-(n-propyl), N-(2-pyrazinylcarbonyl) ethanolamine 2,4,6-trichlorophenylether (a) 2-pyrazine carboxylic acid, 104.3 gm, and 105.9 gm thionyl chloride were added to 800 ml methylene chloride and 5 ml dimethylformamide. The system was heated to reflux, at which point gas evolution took place. The system was stirred at reflux until gas evolution ceased, after about 5 hours, to give the 2-pyrazine carboxylic acid chloride. The solution was cooled to room temperature and transferred to a dropping funnel for use in Step (b) without further isolation.

(b) To a solution of 214.9 gm of N-(n-propyl) ethanolamine 2,4,6-trichlorophenylether, the product of Example 3, and 84.84 gm triethylamine in 800 ml methylene chloride, the acid chloride of Step (a) was added dropwise at room temperature. After the addition was complete, the reaction mixture was stirred 10 minutes. The reaction mixture was then washed with water, then a 5% sodium bicarbonate solution, and then with water again. The mixture was dried over magnesium chloride and stripped to give 254 gm of an oil which solidified upon standing to give a solid with a melting point of 58°–61° C.

Example 5

Preparation of 2,6-dichlorothiophenoxyacetic acid 2,6-dichlorothiophenol, 50 gm, was added to 250 ml of ethanol. 63.8 ml of a 25% solution of sodium methoxide (2 equivalents) in methanol was then added to the system. The system was stirred at room temperature for approximately 3 hours. Afterwards, 20 ml of bromoacetic acid was added and the system then heated to reflux. The system was continued at reflux for 16 hours. The reaction was then stopped and the solvent removed by stripping. The resulting material was dissolved with basic aqueous solution and then washed with methylene chloride. Concentrated HCl was next added to the aqueous solution to acidify it. The product was extracted with methylene chloride. The methylene chloride solution was stripped and triturated with hexane. The product was then filtered, washed with water and air dried to yield 55.3 gm of the title compound.

Example 6

Preparation of N-(n-propyl)-2,6-dichlorothiophenoxyacetamide (a) 2,6-dichlorothiophenoxyacetic acid, 55.3 gm, was added to 250 ml of methylene chloride along with 37.8 gm of carbonyldiimidazole. The system was stirred overnight at room temperature to give the carboxylic acid imidazolide.

(b) 19.1 ml of n-propylamine was then added to the system. The system was then stirred at room temperature for an additional 65 hours. The reaction was stopped and the organic solution was washed first with a dilute HCl solution, then with a sodium bicarbonate solution and then with water. The methylene chloride was removed by stripping to give 33.7 gm of the N-(n-propyl)-2,6-dichlorothiophenoxyacetamide.

Example 7

Preparation of N-(n-propyl) 2-aminoethanethiol 2,6-dichlorophenylthioether

N-(n-propyl)-2,6-dichlorothiophenoxyacetamide, 33.7 gm, was added to 250 ml of tetrahydrofuran. 34.4 ml of borane methyl sulfide (3 equivalents) was then slowly added to the system. The system was heated at approximately 55° C. for 18 hours at which time reaction completion was checked by IR spectroscopy. 200 ml of methanol was then slowly added to the system. After addition of the methanol, the system was acidified by bubbling in HCl gas. Afterwards, the system was refluxed for 1 hour. The solvent was then removed by stripping. The resulting oil was dissolved in methanol which was stripped. The oil was next dissolved in methylene chloride. The organic solution was washed with a sodium hydroxide solution and then with water. The methylene chloride was removed by stripping to give 28.2 gm of the N-(n-propyl) 2-aminoethanethiol 2,6-dichlorophenylthioether.

Example 8

Preparation of N-(n-propyl), N-(3-pyridylcarbonyl) 2-aminoethanethiol 2,6-dichlorophenylthioether (a) 3-pyridine carboxylic acid, 2.5 gm, was added to 10 ml of methylene chloride. 3.2 gm of carbonyldiimidazole was added to the system. The system was stirred at room temperature for 16 hours to give the 3-pyridine carboxylic acid imidazolide.

(b) N-(n-propyl) 2-aminoethanethiol 2,6-dichlorophenylthioether, 5.3 gm, was then added to the system. The system was stirred at room temperature for 24 hours. The reaction was then stopped and the methylene chloride solution was washed with a sodium bicarbonate solution, and then with water. The methylene chloride solution was dried over magnesium sulfate and the methylene chloride removed by stripping to give 3.5 gm of the N-(n-propyl), N-(3-pyridylcarbonyl) 2-aminoethanethiol 2,6-dichlorophenylthioether as a yellow oil, listed as Compound No. 11 in Table I.

Example 9

Preparation of N-(n-propyl)-2,6-dichlorocinnamide (a) 2,6-dichlorocinnamic acid, 50 gm, was added to 500 ml of methylene chloride along with 37.3 gm of carbonyldiimidazole. The system was stirred overnight at room temperature to give the carboxylic acid imidazolide.

(b) 18.9 ml of n-propylamine was then added to the system. The system was then stirred at room temperature for an additional 24 hours. The reaction was stopped and the organic solution washed first with a dilute HCl solution, then with a sodium bicarbonate solution and then with water. The methylene chloride was removed by stripping to give 41.1 gm of the N-(n-propyl)-2,6-dichlorocinnamide.

Example 10

Preparation of N-[3-(2,6-dichlorophenyl)propyl], N-(n-propyl) amine

N-(n-propyl)-2,6-dichlorocinnamide, 41.1 gm, was added to 300 ml of toluene and 12.9 ml of tetrahydrofuran. 63.5 ml of borane methyl sulfide (4 equivalents) was then slowly added to the system. The system was heated at approximately 110° C. for 18 hours at which time reaction completion was checked by IR spectroscopy. 100 ml of methanol was then slowly added to the system. After addition of the methanol, the system was acidified by bubbling in HCl gas. Afterwards, the system was refluxed for 1 hour. The solvent was then removed by stripping. The resulting oil was dissolved in methanol which was stripped. The oil was next dissolved in methylene chloride. The organic solution was washed with a sodium hydroxide solution and then with water. The methylene chloride was removed by stripping to give 41.0 gm of N-[3-(2,6-dichlorophenyl) propyl], N-(n-propyl) amine as a light yellow soft solid.

Example 11

Preparation of N-[3-(2,6-dichlorophenyl)propyl], N-(n-propyl) nicotine amide (a) 3-pyridine carboxylic acid, 2.5 gm, was added to 10 ml of methylene chloride. 3.2 gm of carbonyldiimidazole was added to the system. The system was stirred at room temperature for 18 hours to give the 3-pyridyl carboxylic acid imidazolide.

(b) N-[3-(2,6-dichlorophenyl) propyl], N-(n-propyl) amine, 4.9 gm, was then added to the system. The system was stirred at room temperature for 24 hours. The reaction was then stopped and the methylene chloride solution was washed with a sodium bicarbonate solution and then with water. The methylene chloride solution was dried over magnesium sulfate and the methylene chloride removed by stripping. The residue was chromatographed to give 1.0 gm of the N-[3-(2,6-dichlorophenyl) propyl], N-(n-propyl) nicotine amide. Listed as Compound No. 22 in Table III.

Example 12

Preparation of N-allyl-2,4,6-trichlorophenoxyacetamide (a) 2,4,6-trichlorophenoxyacetic acid, 20.3 gm, was added to 150 ml of methylene chloride along with 13.0 gm of carbonyldiimidazole. The system was stirred overnight at room temperature to give the carboxylic acid imidazolide.

(b) 6.0 ml of allylamine was then added to the system. The system was then stirred at room temperature for an additional 24 hours. The reaction was stopped and the organic solution was washed first with a dilute HCl solution, then with a sodium bicarbonate solution and then with water. The methylene chloride was removed by stripping to give the N-allyl-2,4,6-trichlorophenoxyacetamide.

Example 13

Preparation of N-allyl ethanolamine 2,4,6-trichlorophenylether

N-allyl-2,4,6-trichlorophenoxyacetamide, 14.6 gm, was added to 100 ml of anhydrous tetrahydrofuran. The solution was cooled to about 10° C. with an ice bath. Then lithium aluminum hydride, 1.86 gm, was added slowly. The resulting mixture was stirred in the cold and allowed to warm to room temperature overnight. The mixture was heated at reflux for 6 hours, then again stirred at room temperature overnight. Then 2 ml water, 2 ml of 15% NaOH solution and 6 ml of water were added sequentially. The mixture was filtered through a pad of Celite and the filtrate stripped to yield 10.6 gm of N-allyl ethanolamine 2,4,6-trichlorophenylether as an oil.

Example 14

Preparation of N-allyl, N-(3-pyridylcarbonyl) ethanolamine 2,4,6-trichlorophenylether (a) 3-pyridine carboxylic acid, 3.7 gm, was added to 100 ml of methylene chloride. 4.9 gm of carbonyldiimidazole was added to the system. The system was stirred at room temperature for 16 hours to give the 3-pyridine carboxylic acid imidazolide.

(b) N-allyl ethanolamine 2,4,6-trichlorophenylether, 6.3 gm, was then added to the system. The system was stirred at room temperature for 24 hours. The reaction was then stopped and the methylene chloride solution was washed with a sodium bicarbonate solution and then with water. The methylene chloride solution was dried over magnesium sulfate and the methylene chloride removed by stripping to give the crude N-allyl, N-(3-pyridylcarbonyl) ethanolamine 2,4,6-trichlorophenylether. The product was purified by preparation of a hydrogen chloride salt. Listed as Compound No. 32 in Table IV.

Example 15

Preparation of N-(n-propyl), N-(3-pyridylcarbonyl) ethanolamine 2,4,6-trichlorophenylether

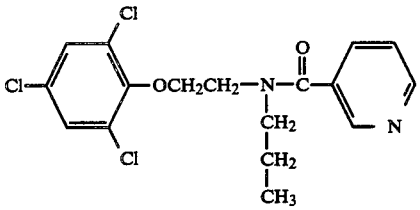

(a) 3-pyridine carboxylic acid, 3.1 gm, was added to 50 ml of methylene chloride. 4.0 gm of carbonyldiimidazole was added to the system. The system was stirred at room temperature for 2 hours to form the 3-pyridine carboxylic acid imidazolide.

(b) N-(n-propyl) ethanolamine 2,4,6-trichlorophenylether, 6.3 gm, was then added to the system. The system was stirred at room temperature for 18 hours. The reaction was then stopped and the methylene chloride was washed with a sodium bicarbonate solution and then with water. The methylene chloride solution was dried over magnesium sulfate and the methylene chloride removed by stripping to give 3.0 gm of the N-(n-propyl), N-(3-pyridinylcarbonyl) ethanolamine 2,4,6-trichlorophenylether. If desired, the crude compound may be further purified by recrystallization from hexane. Listed as Compound No. 1 in Table I.

Example 15a

Preparation of N-(n-propyl), N-(3-pyridylcarbonyl) ethanolamine 2,4,6-trichlorophenylether (a) 3-pyridine carboxylic acid, 338 gm (2.75 moles) and 446 gm (2.75 moles) of carbonyldiimidazole were combined in 2.5 l methylene chloride. The system was heated gradually to reflux and stirred for a total of 1½ hours, at which time the system temperature was at methylene chloride reflux and carbon dioxide evolution had ceased, to give the 3-pyridine carboxylic acid imidazolide. (b) To the above methylene chloride solution, 777 gm (2.75 moles) N-(n-propyl) ethanolamine 2,4,6-trichlorophenylether, the product of Example 3, was added and the system stirred at a gentle reflux over the weekend. The reaction was then stopped and the methylene chloride solution washed sequentially with water, then 5% HCl, then water, then 5% sodium bicarbonate solution, and then water again. The methylene chloride solution was dried over magnesium sulfate and stripped to give 775 gm of crude product, a yellow cake. The crude product was recrystallized from isopropyl alcohol (about 2 ml per gm crude product) to give a white solid with a melting point of 104°–106° C.

Elemental analysis for $C_{17}H_{17}N_2O_2Cl_3$ showed: calculated % C 52.6, % H 4.4, and % N 7.2; found % C 52.13, H 4.65, and % N 7.16.

Example 16

Preparation of N-(n-propyl), N-(5-pyrimidylcarbonyl) ethanolamine 2,4,6-trichlorophenylether

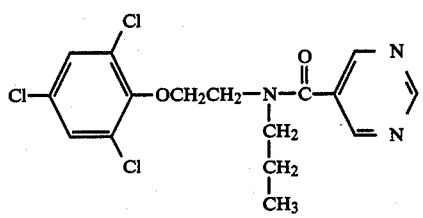

(a) 5-pyrimidyl carboxylic acid, 1.9 gm, was added to 30 ml of methylene chloride. 2.4 gm of carbonyldiimidazole was added to the system. The system was stirred at room temperature for 3 hours to form the 5-pyrimidyl carboxylic acid imidazolide.

(b) N-(n-propyl) ethanolamine 2,4,6-trichlorophenylether, 4.2 gm, was then added to the system. The system was stirred at room temperature for 18 hours. The reaction was then stopped and the methylene chloride was washed with a sodium bicarbonate solution, then with dilute HCl (pH about 3) and then with water. The methylene chloride solution was dried over magnesium sulfate and the methylene chloride removed by stripping to give 3.1 gm of the N-(n-propyl), N-(5-pyrimidylcarbonyl) ethanolamine 2,4,6-trichlorophenylether. Listed as Compound No. 2 in Table I.

Example 17

Preparation of N-(n-propyl), N-(1-methyl-5-imidazolylcarbonyl) ethanolamine 2,4,6-trichlorophenylether

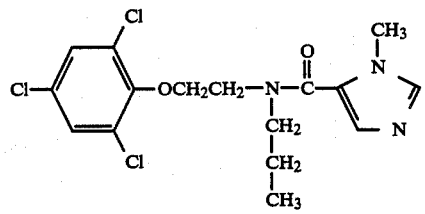

(a) 1-methyl-5-imidazole carboxylic acid, 7.0 gm, was added to 50 ml of methylene chloride. 5.2 gm of carbonyldiimidazole was added to the system. The system was stirred at room temperature for 18 hours to give the 1-methyl-5-imidazolyl carboxylic acid imidazolide.

(b) N-(n-propyl) ethanolamine 2,4,6-trichlorophenylether, 5.6 gm, was then added to the system. The system was stirred at room temperature for 24 hours. The reaction was then stopped and the methylene chloride was washed with a sodium bicarbonate solution and then with water. The methylene chloride solution was dried over magnesium sulfate and the methylene chloride removed by stripping to give 3.8 gm of the N-(n-propyl), N-(1-methyl-5-imidazolylcarbonyl) ethanolamine 2,4,6-trichlorophenylether. Listed as Compound No. 12 in Table I.

Example 18

Preparation of N-(n-propyl), N-(3-pyridylthiocarbonyl) ethanolamine 2,4,6-trichlorophenylether

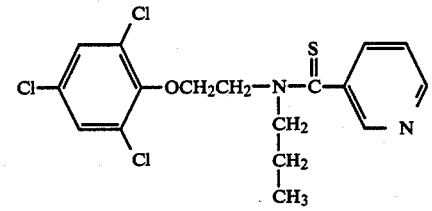

N-(n-propyl), N-(3-pyridylcarbonyl) ethanolamine 2,4,6-trichlorophenylether, 7.8 gm, was dissolved in 50 ml of tetrahydrofuran. 4.4 gm of phosphorus pentasulfide ($P_2S_5$) was added to the system. The system was exposed throughout to microwave radiation in order to aid in the dispersion of the phosphorus pentasulfide. The system was stirred at about 10° C. for 1 hour. Then an additional 4.4 gm of $P_2S_5$ was added to the system and the reaction continued for an additional 3 hours. Afterwards, the system was filtered; the solvent was removed by stripping and the residue chromatographed to give 2.1 gm of the N-(n-propyl), N-(3-pyridylthiocarbonyl) ethanolamine 2,4,6-trichlorophenylether. Listed as Compound No. 17 in Table I.

Example 19

Preparation of 2-hydroxy acetone 2,4,6-trichlorophenylether

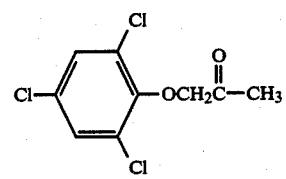

A stirred mixture of 39.4 gm (0.2 moles) 2,4,6-trichlorophenol, 17.6 ml (0.2 moles) 90% chloroacetone and 45.6 ml (0.2 moles) 25% sodium methoxide in methanol in 200 ml ethanol was heated to reflux and refluxed overnight. The reaction was then stopped and the solvent stripped. The residue was then taken up in methylene chloride. The organic solution was washed first with dilute sodium hydroxide and then water. The methylene chloride was stripped and the residue dried under vacuum to give 42.7 gm of product, a brown solid.

Example 20

Preparation of N-(n-propyl) 2-aminopropanol 2,4,6-trichlorophenylether

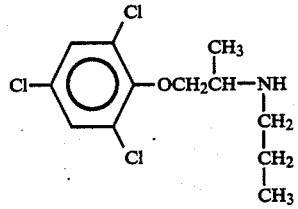

To a stirred mixture of 12 gm (0.048 moles) of the product of Example 19 in methanol (about 50 ml), 19.7 ml (0.24 moles) n-propylamine and 2.3 gm (0.036 moles) sodium cyanoborohydride were added. To that mixture a few grams of 3A molecular sieve were added to scavenge water. Hydrogen chloride was bubbled through the mixture until the pH was about 5–6. The reaction mixture was then allowed to stir at room temperature over the weekend. After filtering off the solids, the filtrate was stripped. The residue was taken up in methylene chloride. The methylene chloride solution was basified with 50% sodium hydroxide and then washed twice with water. The methylene chloride was filtered off through magnesium sulfate. Stripping and drying gave 8.0 gm of the product, a brown oil.

Elemental analysis for $C_{12}H_{16}NOCl_3$ showed: calculated % C 48.60, % H 5.39, and % N 4.72; found % C 48.14, H 5.81, and % N 4.13.

Example 21

Preparation of N-(n-propyl), N-(3-pyridylcarbonyl) propanol-2-amine 2,4,6-trichlorophenylether

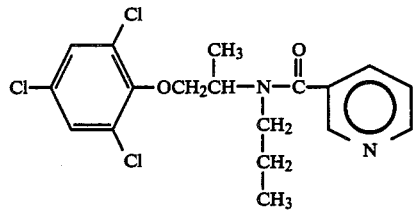

(a) Nicotinic acid, 1.1 gm, was added to 10 ml chloroform. To that mixture, 1.5 gm carbonyldiimidazole was added. The resulting mixture was then stirred at room temperature overnight to give nicotinic acid imidazolide.

(b) The product of Example 20, 2.8 gm, was then added to the system and the resulting mixture was heated to light reflux and stirred for about 18 hours. The reaction was then stopped and the chloroform solution was washed with a sodium bicarbonate solution and then with water. The chloroform solution was filtered off through magnesium sulfate, and the chloroform removed by stripping. Drying of the residue under vacuum gave 2.6 gm of the product, a brown oil, listed as Compound No. 20 in Table I.

Elemental analysis for $C_{18}H_{19}N_2O_2Cl_3$ showed: calculated % C 53.81, % H 4.73, and % N 6.97; found % C 51.61, H 5.08, and % N 7.05.

Example 22

Preparation of N-(n-propyl), N-(2-pyrazinylcarbonyl) propanol-2-amine 2,4,6-trichlorophenylether

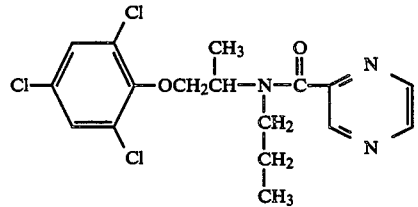

(a) 2-pyrazine carboxylic acid, 1.3 gm was added to 10 ml chloroform. 1.7 gm of carbonyldiimidazole was added to the system. The system was stirred overnight at room temperature to give the 2-pyrazine carboxylic acid imidazolide.

(b) 3.1 gm of the product of Example 20 was then added to the system. The system was heated to light reflux and stirred at reflux overnight. The reaction was then stopped, and the chloroform solution was washed with a sodium bicarbonate solution and then with water. The chloroform was filtered through magnesium sulfate, stripped and the residue dried under vacuum to give 2.8 gm of the product, a brown oil, listed as Compound No. 21 in Table I.

Elemental analysis for $C_{17}H_{18}N_3O_2Cl_3$ showed: calculated: % C 50.69, % H 4.47 and % N 10.44; found % C 49.73, % H 4.72, and % N 9.81.

By following the procedures of Examples 1 to 22 and using the appropriate starting materials and reagents, the following compounds are prepared:

N-(n-propyl), N-(2-pyrazinylcarbonyl) ethanolamine 2,4,6-trichlorophenylether;

N-(n-propyl), N-(3-pyridylcarbonyl) ethanolamine 2,4,6-trichlorophenylether;

N-(n-propyl), N-(5-pyrimidylcarbonyl) ethanolamine 2,4,6-trichlorophenylether;

N-(n-propyl), N-(1-methyl-5-imidazolylcarbonyl) ethanolamine 2,4,6-trichlorophenylether;

N-(n-propyl), N-(5-pyrimidylcarbonyl) ethanolamine 4-t-butylphenylether;

N-allyl, N-(3-pyridylcarbonyl) ethanolamine 2,4,6-trichlorophenylether;

N-(2-chloroallyl), N-(3-pyridylcarbonyl) ethanolamine 2,6-dichlorophenylether;

N-(2-bromoallyl), N-(5-pyrimidylcarbonyl) ethanolamine 4-t-butylphenylether;

N-(methoxyethyl), N-(3-pyridylcarbonyl) ethanolamine 2,4,6-trichlorophenylether;

N-(ethoxyethyl), N-(3-pyridylcarbonyl) ethanolamine 2,4,6-tribromophenylether;

N-(ethoxyethyl), N-(3-pyridylcarbonyl) ethanolamine 2,4,6-triiodophenylether;

N-(methylthioethyl), N-(3-pyridylcarbonyl) ethanolamine 2,4,6-trichlorophenylether;

N-propargyl, N-(3-pyridylcarbonyl) ethanolamine 4-t-butylphenylether;

N-chloromethyl, N-(5-pyrimidylcarbonyl) ethanolamine phenylether;

N-bromomethyl, N-(2-pyrazinylcarbonyl) ethanolamine 4-methylphenylether;

N-(2,2,2-trichloroethyl), N-(3-pyridylcarbonyl) ethanolamine 4-ethylphenylether;

N-(ethylthioethyl), N-(3-pyridylcarbonyl) ethanolamine 2,6-dimethylphenylether;

N-(2-hydroxyethyl), N-(1-methyl-5-imidazolycarbonyl) ethanolamine phenylether;

N-(n-propyl), N-(3-pyridylcarbonyl) 3-amino-1-propanol 2,4,6-trichlorophenylether;

N-(n-propyl), N-(3-pyridylcarbonyl) 3-amino-2-methyl-1-propanol 2,4,6-trichlorophenylether;

N-(n-propyl), N-(3-pyridylcarbonyl) 4-amino-1-butanol 2,4,6-trichlorophenylether;

N-(n-propyl), N-(3-pyridylcarbonyl) 4-amino-3,3-dimethyl-1-butanol 2,4,6-trichlorophenylether;

N-(n-propyl), N-(3-pyridylcarbonyl) 4-amino-3-ethyl-1-butanol 2,4,6-trichlorophenylether;

N-allyl, N-(2-pyrazinylcarbonyl) 4-amino-2,3-dimethyl-1-butanol 2,4,6-trichlorophenylether;

N-(n-propyl), N-(3-pyridylthiocarbonyl) ethanolamine 2,4,6-trichlorophenylether;

N-(n-propyl), N-(2-pyrazinylthiocarbonyl) ethanolamine 4-t-butylphenylether;
N-(2-chloroethyl), N-(5-pyrimidylthiocarbonyl) ethanolamine 2,4,6-trimethylphenylether;
N-(n-propyl), N-(3-pyridylcarbonyl) ethanolamine 4-trifluoromethylphenylether;
N-(n-propyl), N-(2-pyrazinylcarbonyl) 2-aminoethanethiol 2,4,6-trichlorophenylthioether;
N-(n-propyl), N-(3-pyridylcarbonyl) 2-aminoethanethiol 2,4,6-trichlorophenylthioether;
N-(n-propyl), N-(5-pyrimidylcarbonyl) 2-aminoethanethiol 2,4,6-tribromophenylthioether;
N-(n-propyl), N-(1-methyl-5-imidazolylcarbonyl) 2-aminoethanethiol 2,4,6-trichlorophenylthioether;
N-(n-propyl), N-(5-pyrimidylcarbonyl) 2-aminoethanethiol 4-t-butylphenylthioether;
N-allyl, N-(3-pyridylcarbonyl) 2-aminoethanethiol 2,4,6-trichlorophenylthioether;
N-(2-chloroallyl), N-(3-pyridylcarbonyl) 2-aminoethanethiol 2,6-dichlorophenylthioether;
N-(2-bromoallyl), N-(5-pyrimidylcarbonyl) 2-aminoethanethiol 4-t-butylphenylthioether;
N-(methoxyethyl), N-(3-pyridylcarbonyl) 2-aminoethanethiol 2,4,6-trichlorophenylthioether;
N-(ethoxyethyl), N-(1-methyl-5-imidazolylcarbonyl) 2-aminoethanethiol 2,4,6-tribromophenylthioether;
N-(ethoxyethyl), N-(1-methyl-5-imidazolylcarbonyl) 2-aminoethanethiol 2,4,6-triiodophenylthioether;
N-(methylthioethyl), N-(3-pyridylcarbonyl) 2-aminoethanethiol 2,4,6-trichlorophenylthioether;
N-propargyl, N-(3-pyridylcarbonyl) 2-aminoethanethiol 4-t-butylphenylether;
N-chloromethyl, N-(5-pyrimidylcarbonyl) 2-aminoethanethiol phenylthioether;
N-bromomethyl, N-(2-pyrazinylcarbonyl) 2-aminoethanethiol 4-methylphenylthioether;
N-(2,2,2-trichloroethyl), N-(3-pyridylcarbonyl) 2-aminoethanethiol 4-ethylphenylthioether;
N-(ethylthioethyl), N-(3-pyridylcarbonyl) 2-aminoethanethiol 2,6-dimethylphenylthioether;
N-(2-hydroxyethyl), N-(1-methyl-5-imidazolylcarbonyl) 2-aminoethanethiol phenylthioether;
N-(n-propyl), N-(3-pyridylcarbonyl)-3-amino-1-propanethiol 2,4,6-trichlorophenylthioether;
N-(n-propyl), N-(3-pyridylcarbonyl)-3-amino-2-methyl-1-propanethiol 2,4,6-trichlorophenylthioether;
N-(n-propyl), N-(3-pyridylcarbonyl)-4-amino-1-butanethiol 2,4,6-trichlorophenylthioether;
N-(n-propyl), N-(3-pyridylcarbonyl)-4-amino-3,3-dimethyl-1-butanethiol 2,4,6-trichlorophenylthioether;
N-(n-propyl), N-(3-pyridylcarbonyl)-4-amino-3-ethyl-1-butanethiol 2,4,6-trichlorophenylether;
N-allyl, N-(2-pyrazinylcarbonyl)-4-amino-2,3-dimethyl-1-butanethiol 2,4,6-trichlorophenylthioether;
N-(n-propyl), N-(3-pyridylthiocarbonyl) 2-aminoethanethiol 4-t-butylphenylthioether;
N-(n-propyl), N-(2-pyrazinylthiocarbonyl) 2-aminoethanethiol 2,4,6-trichlorophenylthioether;
N-(2-chloroethyl), N-(5-pyrimidylthiocarbonyl) 2-aminoethanethiol 2,4,6-trimethylphenylthioether;
N-(n-propyl), N-(3-pyridylcarbonyl) 2-aminoethanethiol 4-trifluoromethylphenylthioether;
N-[3-(2,4,6-trichlorophenyl) propyl], N-(n-propyl) nicotine amide;
N-[3-(2,4,6-trichlorophenyl) propyl], N-(n-propyl) pyrazinamide;
N-[3-(2,4,6-tribromophenyl) propyl], N-(n-propyl) nicotine amide;
N-[3-(2,4,6-trichlorophenyl) propyl], N-allyl nicotine amide;
N-[3-(4,6-dichlorophenyl) propyl], N-(2-chloroallyl) nicotine amide;
N-[3-(2,4,6-trichlorophenyl) propyl], N-(methoxymethyl) nicotine amide;
N-[3-(2,4,6-trichlorophenyl) propyl], N-(methylthiomethyl) nicotine amide;
N-[3-(4-t-butylphenyl) propyl], N-propargyl-nicotine amide;
N-(3-phenylpropyl), N-chloromethylpyrazinamide;
N-[3-(4-methylphenyl) propyl], N-bromomethylpyrazinamide;
N-[3-(2,6-dimethylphenyl) propyl], N-(2,2,2-trichloroethyl) nicotine amide;
N-[3-(4-ethylphenyl) propyl], N-ethylthioethyl-nicotine amide;
N-[4-(2,4,6-trichlorophenyl) butyl], N-(n-propyl) nicotine amide;
N-[5-(2,4,6-trichlorophenyl) pentyl], N-(n-propyl) nicotine amide;
N-[2-methyl-4-(2,4,6-trichlorophenyl) butyl], N-(n-propyl) nicotine amide;
N-[2,3-dimethyl-4-(2,4,6-trichlorophenyl) butyl], N-(n-propyl) nicotine amide;
N-[3-(2,4,6-trichlorophenyl) propyl], N-(n-propyl) nicotine thioamide;
N-[3-(4-t-butylphenyl) propyl], N-(n-propyl) pyrazinthioamide;
N-[3-(4-trifluoromethylphenyl) propyl], N-(n-propyl) nicotine amide;
N-[3-(4-trifluoromethylphenyl) propyl], N-allyl pyrazinamide;
N-(n-propyl, N-(3-pyridylcarbonyl) ethanolamine 2,6-dichlorophenylether;
N-(n-propyl), N-(5-pyrimidylcarbonyl) ethanolamine 2,6-dichlorophenylether; and
N-(n-propyl), N-(2-pyrazinylcarbonyl) ethanolamine 2,6-dichlorophenylether.

Example A

Bean Powdery Mildew

The compounds of the invention were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results are tabulated in Table V.

Example B

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table V.

Example C

Celery Late Blight

The Celery Late Blight tests were conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table V.

Example D

Tomato Early Blight

Compounds of the invention were tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The compounds tested and the results are tabulated in Table V.

Example E

Grape Downy Mildew

The compounds of the invention were tested for the control of the Grape Downy Mildew organism *Plasmopara viticola*. Detached leaves, between 70 mm and 85 mm in diameter, 7-week-old *Vitis vinifera* cultivar Emperor grape seedlings were used as hosts. The leaves were sprayed with a 250-ppm solution of the test compound in acetone. The sprayed leaves were dried, inoculated with a spore suspension of the organism, placed in a humid environmental chamber and incubated at 66° F. to 68° F. and about 100% relative humidity. After incubation for 2 days, the plants were then held in a greenhouse 7 to 9 days; then the amount of disease control was determined. The percent disease control provided by a given test compound was based on the percent disease reduction relative to untreated check plants. The results are tabulated in Table V.

Example F

Leaf Rust

The Leaf Rust test was made using pinto beans. The pathogen was *Uromyces phaseoli tipica*. The pinto bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° F. to 70° F. The plants were then removed from the chamber, allowed to dry, and then maintained in a greenhouse at a 60% to 80% relative humidity. The rate of infection on the leaves was made after about 14 days. The percent disease control provided by a given test compound was based on the percent disease reduction relative to untreated check plants. The results are reported in Table V.

Example G

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a non-ionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 \times \left( \frac{\% \text{ disease in treated plants}}{\% \text{ disease in check}} \right)$$

The results are tabulated in Table V.

TABLE I

Compounds Of The Formula:

$$R-X-CH_2CH_2-N(-CR^2=Z)-CH_2-CH_2-CH_3$$

| Compound No. | Z | X | R | R² | Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|---|
| 1 | O | O | 2,4,5-trichlorophenyl | 3-pyridyl | 52.66 | 51.46 | 4.42 | 4.34 | 7.23 | 7.41 | light brown solid | 80°–82° C. |
| 2 | O | O | 2,4,5-trichlorophenyl | pyrimidinyl | 49.44 | 49.04 | 4.15 | 4.26 | 10.81 | 10.19 | light yellow solid | 68°–73° C. |
| 3 | O | O | 2,4,5-trichlorophenyl | pyrazinyl | 49.44 | 47.35 | 4.15 | 4.09 | 10.81 | 9.92 | oil | |
| 4 | O | O | 2,6-dichlorophenyl | 3-pyridyl | 57.79 | 57.55 | 5.14 | 5.32 | 7.93 | 7.91 | oil | |
| 5 | O | O | 4-t-butylphenyl | pyrazinyl | 70.35 | 68.33 | 7.97 | 8.40 | 12.31 | 11.47 | oil | |
| 6 | O | O | 4-t-butylphenyl | 3-pyridyl | 74.08 | 72.24 | 8.29 | 9.13 | 8.23 | 7.30 | oil | |
| 7 | O | O | 2,4-dichlorophenyl | pyrazinyl | 54.24 | 52.28 | 4.84 | 4.88 | 11.86 | 11.37 | oil | |
| 8 | O | O | 2,4-dichlorophenyl | 3-pyridyl | 57.79 | 54.83 | 5.14 | 5.52 | 7.93 | 7.25 | oil | |

TABLE I-continued

Compounds Of The Formula:

$$R-X-CH_2CH_2-N(-CR^2=Z)-CH_2-CH_2-CH_3$$

| Compound No. | Z | X | R | R² | Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|---|
| 9 | O | O | 2,4,5-trichlorophenyl | 2-pyridyl | 52.66 | 52.18 | 4.42 | 5.12 | 7.23 | 6.10 | oil | |
| 10 | O | O | 2,4,5-trichlorophenyl | 4-pyridyl | 52.66 | 52.63 | 4.42 | 5.32 | 7.23 | 5.87 | oil | |
| 11 | O | S | 2,6-dichlorophenyl | 3-pyridyl | 55.28 | 55.71 | 4.91 | 5.16 | 7.59 | 7.74 | oil | |
| 12 | O | O | 2,4,5-trichlorophenyl | 1-methylimidazol-2-yl | 49.18 | 48.00 | 4.64 | 5.19 | 10.75 | 9.36 | oil | |
| 13 | O | O | 2,6-dichlorophenyl | pyrimidin-5-yl | 54.24 | 53.93 | 4.84 | 5.00 | 11.86 | 12.40 | light yellow solid | 60°–62° C. |
| 14 | O | O | 2,4,6-trimethylphenyl | 3-pyridyl | 73.58 | 74.00 | 8.03 | 8.79 | 8.58 | 8.70 | oil | |
| 15 | O | O | 2,4,6-trimethylphenyl | pyrazin-2-yl | 69.69 | 69.96 | 7.69 | 8.39 | 12.83 | 12.95 | oil | |

TABLE I-continued

Compounds Of The Formula:

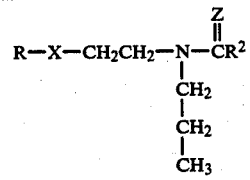

| Compound No. | Z | X | R | R² | ANALYSIS Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|---|
| 16 | O | O | mesityl (2,4,6-trimethylphenyl) | pyrazinyl | 69.69 | 70.97 | 7.69 | 8.17 | 12.83 | 12.61 | oil | |
| 17 | S | O | 2,4,5-trichlorophenyl | pyridyl | 50.56 | 53.46 | 4.24 | 5.08 | 6.94 | 6.23 | oil | |
| 18 | S | O | 2,4,5-trichlorophenyl | pyrazinyl | 47.47 | 46.80 | 3.98 | 3.95 | 10.38 | 10.14 | yellow solid | 85°–87° C. |

TABLE II

Compounds Of The Formula:

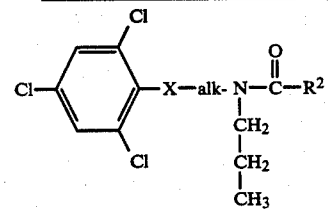

| Compound No. | X | alk | R² | ANALYSIS Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|
| 19 | O | —CH₂CH₂CH₂— | pyridyl | 53.81 | 58.33 | 4.77 | 5.67 | 6.97 | 8.00 | oil | |
| 20 | O | —CH₂CH(CH₃)— | pyridyl | 53.81 | 51.61 | 4.73 | 5.08 | 6.97 | 7.05 | brown oil | |
| 21 | O | —CH₂CH(CH₃)— | pyrazinyl | 50.69 | 49.73 | 4.47 | 4.72 | 10.44 | 9.81 | brown oil | |

TABLE III

Compounds Of The Formula

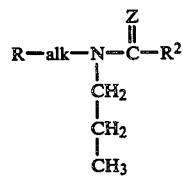

| Compound No. | Z | alk | R | R² | Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|---|
| 22 | O | —CH₂CH₂CH₂— | 2,6-Cl₂-C₆H₃ | 3-pyridyl | 61.54 | 58.42 | 5.94 | 6.18 | 7.98 | 7.04 | oil | |
| 23 | O | —CH₂CH(CH₃)CH₂— | 4-(CH₃)₃C-C₆H₄ | 3-pyridyl | 78.36 | 67.43 | 9.15 | 8.55 | 7.95 | 6.34 | oil | |
| 24 | O | —CH₂CH(CH₃)CH₂— | 4-(CH₃)₃C-C₆H₄ | 2-pyrazinyl | 74.75 | 67.52 | 8.84 | 8.33 | 11.89 | 8.38 | oil | |
| 25 | O | —CH₂CH₂CH₂— | 2,6-Cl₂-C₆H₃ | 2-pyrazinyl | 57.96 | 56.52 | 5.44 | 5.95 | 11.93 | 11.00 | oil | |
| 26 | O | —CH₂CH₂CH₂— | 2,4-Cl₂-C₆H₃ | 2-pyrazinyl | 57.96 | 55.44 | 5.44 | 5.64 | 11.93 | 11.35 | oil | |
| 27 | O | —CH₂CH₂CH₂— | 2,4-Cl₂-C₆H₃ | 3-pyridyl | 61.54 | 58.56 | 5.74 | 5.99 | 7.98 | 7.72 | oil | |
| 28 | O | —CH₂— | 2,6-Cl₂-C₆H₃ | 2-pyrazinyl | 55.56 | 56.14 | 4.66 | 4.97 | 12.96 | 14.51 | yellow solid | 83°–85° C. |
| 29 | O | —CH₂— | 2,6-Cl₂-C₆H₃ | 3-pyridyl | 59.47 | 59.08 | 4.95 | 5.06 | 8.67 | 8.98 | yellow solid | 93°–95° C. |

TABLE IV

Compounds Of The Formula:

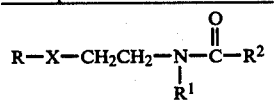

| Compound No. | X | R¹ | R | R² | Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|---|
| 30 | O | —CH₂CH₂OH | 2,4,6-trichlorophenyl | 3-pyridyl | 49.31 | 48.31 | 3.88 | 3.81 | 7.19 | 6.37 | oil | |
| 31 | O | —CH₂CH₂OH | 2,4,6-trichlorophenyl | pyrazinyl | 46.11 | 46.12 | 3.61 | 3.68 | 10.76 | 10.48 | oil | |
| 32 | O | —CH₂CH=CH₂ | 2,4,6-trichlorophenyl | 3-pyridyl | 52.94 | 51.62 | 3.92 | 3.56 | 7.26 | 6.45 | oil | |
| 33 | O | —CH₂CH₂OCH₂CH₃ | 2,4,6-trichlorophenyl | 3-pyridyl | 51.75 | 52.70 | 4.58 | 4.76 | 6.71 | 6.82 | oil | |
| 34 | O | —CH₂CH₂OCH₂CH₃ | 2,4,6-trichlorophenyl | pyrazinyl | 48.76 | 49.05 | 4.33 | 4.46 | 10.03 | 10.33 | oil | |
| 35 | O | —CH₂CH₃ | 2,4,6-trichlorophenyl | 4-pyridyl | 51.45 | 49.98 | 4.05 | 3.86 | 7.50 | 7.52 | oil | |
| 36 | O | —CH₂CH₃ | 2,4,6-trichlorophenyl | pyrazinyl | 48.08 | 46.43 | 3.77 | 3.81 | 11.21 | 10.07 | oil | |

TABLE V

| Compound No. | Fungicidal Activity % Control | | | | | | |
|---|---|---|---|---|---|---|---|
| | GDM | TLB | CLB | TEB | BR | BPM | RB |
| 1 | 50 | 0 | 46 | 96 | 0 | 100 | 86 |
| 2 | 3 | 0 | 93 | 98 | 0 | 100 | 38 |
| 3 | 13 | 0 | 62 | 94 | 19 | 100 | 75 |
| 4 | 17 | 0 | 38 | 96 | 0 | 100 | 90 |

TABLE V-continued

| Compound No. | Fungicidal Activity % Control | | | | | | |
|---|---|---|---|---|---|---|---|
| | GDM | TLB | CLB | TEB | BR | BPM | RB |
| 5 | 28 | 0 | 17 | 36 | 0 | 94 | — |
| 6 | 0 | 10 | 0 | 50 | 0 | 98 | — |
| 7 | 13 | 0 | 15 | 0 | 3 | 21 | 0 |
| 8 | 0 | 0 | 45 | 40 | 3 | 50 | 0 |
| 9 | 19 | 0 | 9 | 0 | 50 | 0 | 10 |
| 10 | 9 | 11 | 0 | 32 | 29 | 0 | 0 |
| 11 | 13 | 0 | 0 | 60 | 0 | 58 | 29 |
| 12 | 19 | 18 | 45 | 36 | 29 | 100 | 0 |
| 13 | 10 | 4 | 80 | 97 | 0 | 81 | — |
| 14 | 0 | 0 | 85 | 67 | 0 | 100 | 64 |
| 15 | 0 | 0 | 15 | 67 | 0 | 44 | 29 |
| 16 | 7 | 0 | 38 | 83 | 0 | 50 | 36 |
| 17 | 4 | 0 | 62 | 87 | 0 | 100 | 100 |
| 18 | 43 | 0 | 85 | — | 0 | 54 | — |
| 19 | 30 | 10 | 38 | 0 | 0 | 70 | 96 |
| 20 | 7 | 0 | 0 | — | 23 | 93 | 0 |
| 21 | 67 | 0 | 0 | — | 23 | 71 | 0 |
| 22 | 7 | 0 | 38 | 88 | 0 | 44 | 0 |
| 23 | 0 | 7 | 29 | 33 | 0 | 100 | 0 |
| 24 | 7 | 4 | 17 | 8 | 0 | 72 | 0 |
| 25 | 0 | 0 | 8 | 29 | 0 | 28 | 0 |
| 26 | 13 | 4 | 10 | 0 | 3 | 11 | 21 |
| 27 | 0 | 0 | 35 | 57 | 3 | 82 | 71 |
| 28 | 3 | 4 | 30 | 27 | 7 | 92 | 0 |
| 29 | 27 | 0 | 0 | 50 | 0 | 48 | — |
| 30 | 54 | 7 | 32 | 17 | 0 | 33 | 0 |
| 31 | 29 | 0 | 0 | 42 | 0 | 0 | 0 |
| 32 | 41 | 0 | 0 | 0 | 0 | 4 | 0 |
| 33 | 18 | 0 | 54 | 52 | 0 | 88 | 0 |
| 34 | 7 | 0 | 15 | 0 | 0 | 0 | 38 |
| 35 | 41 | 0 | 98 | 30 | 0 | 100 | 96 |
| 36 | 45 | 0 | 50 | 0 | 0 | 75 | 0 |

GDM - Grape Downy Mildew (*Plasmopara viticola*)
TLB - Tomato Late Blight (*Phytophthora infestans*)
CLB - Celery Late Blight (*Septoria apii*)
TEB - Tomato Early Blight (*Alternaria solani conidia*)
BR - Bean Rust (*Uromyces phaseoli tipica*)
BPM - Bean Powdery Mildew (*Erysiphe polygoni*)
RB - Rice Blast (*Piricularia oryzae*)

What is claimed is:

1. A compound of the formula:

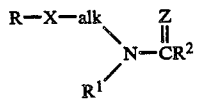

$$R-X-alk \diagdown_{R^1}^{} N-\overset{Z}{\overset{\|}{C}}R^2$$

wherein R is phenyl, or phenyl substituted with 1 to 3 substituents independently selected from fluoro, chloro, bromo, iodo, nitro, lower alkyl, lower alkoxy, lower alkyl or lower alkoxy substituted with 1 to 3 of the same or different halogens; $R^1$ is lower alkyl, or —$CH_2Y$ wherein Y is lower alkenyl, lower alkenyl substituted with 1 to 3 of the same or different halogens, lower alkynyl, lower alkynyl substituted with 1 to 3 of the same or different halogens, lower alkoxyalkyl, lower alkoxy, lower alkylthioalkyl, lower thioalkyl, lower hydroxyalkyl, lower haloalkyl, or halogen; $R^2$ is a 6-membered aromatic heterocyclic ring containing 2 ring nitrogen atoms and the remainder carbon atoms, or a 6-membered aromatic heterocyclic ring containing 2 ring nitrogen atoms and the remainder carbon atoms with the ring substituted with 1 to 2 independent lower alkyl groups, with the proviso that a nitrogen of the 6-membered heterocyclic ring is not bonded to the

$$\overset{Z}{\overset{\|}{-C-}}$$

group; Z is sulfur, or oxygen; X is sulfur, oxygen, or represents a direct linkage between R and alk; and alk is a branched- or straight-chain alkylene group of 1 to 10 carbons with the proviso that the chain length is no longer than 5 carbons.

2. A compound of the formula defined in claim 1 wherein $R^2$ is pyrazinyl or pyrimidyl.

3. A compound of the formula defined in claim 1 wherein R is phenyl substituted with 1 to 3 halogens; $R^1$ is lower alkyl, lower alkenyl, lower alkoxyalkyl or hydroxy; $R^2$ is pyrazinyl or pyrimidyl and alk is ethylene or isopropylene.

4. A compound of the formula defined in claim 1 wherein $R^2$ is pyrazinyl.

5. A compound of the formula defined in claim 1 wherein $R^1$ is lower alkyl or $CH_2Y$ wherein Y is lower alkenyl, lower alkynyl, lower alkoxyalkyl, lower alkoxy, lower hydroxyalkyl, lower haloalkyl or halogen.

6. A compound of the formula described in claim 5 wherein $R^1$ is lower alkyl.

7. A compound of the formula defined in claim 6 wherein $R^1$ is n-propyl.

8. A compound of the formula defined in claim 6 wherein $R^1$ is ethyl.

9. A compound of the formula defined in claim 1 wherein R is phenyl substituted with 1 to 3 substituents selected from fluoro, chloro, bromo, iodo, nitro, lower alkyl, lower alkoxy or lower alkyl substituted with 1 to 3 halogens.

10. A compound of the formula defined in claim 9 wherein R is phenyl substituted with 1 to 3 halogens.

11. A compound of the formula defined in claim 10 wherein R is 2,4,6-trihalophenyl.

12. A compound of the formula defined in claim 11 wherein R is 2,4,6-trichlorophenyl.

13. A compound of the formula defined in claim 10 wherein R is 2,6-dihalophenyl.

14. A compound of the formula defined in claim 13 wherein R is 2,6-dichlorophenyl.

15. A compound of the formula defined in claim 10 wherein X is sulfur or oxygen.

16. A compound of the formula defined in claim 1 wherein $R^2$ is 2-pyrazyl.

17. A compound of the formula defined in claim 1 wherein $R^2$ is 5-pyrimidyl.

18. A compound of the formula defined in claim 1 wherein alk is isopropylene.

19. A compound of the formula defined in claim 1 wherein alk is ethylene.

20. A compound of the formula defined in claim 19 wherein $R^1$ is n-propyl.

21. A compound of the formula defined in claim 20 wherein R is 2,4,6-trichlorophenyl.

22. A compound of the formula defined in claim 20 wherein R is 2,6-dichlorophenyl.

23. A compound of the formula defined in claim 21 wherein X and Z are oxygen.

24. A compound of the formula defined in claim 23 wherein $R^2$ is 2-pyrazyl.

25. A compound of the formula described in claim 21 wherein X is oxygen and Z is sulfur.

26. A compound of the formula described in claim 22 wherein X and Z are oxygen.

27. A compound of the formula described in claim 26 wherein $R^2$ is 5-pyrimidyl.

28. A fungicidal composition comprising a biologically inert carrier and a fungicidally effective amount of a compound of the formula defined in claim 1.

29. A fungicidal composition comprising a biologically inert carrier and a fungicidally effective amount of a compound of the formula defined in claim 5.

30. A fungicidal composition comprising a biologically inert carrier and a fungicidally effective amount of a compound of the formula defined in claim 9.

31. A fungicidal composition comprising a biologically inert carrier and a fungicidally effective amount of a compound of the formula defined in claim 2.

32. A fungicidal composition comprising a biologically inert carrier and a fungicidally effective amount of a compound of the formula defined in claim 21.

33. A fungicidal composition comprising a biologically inert carrier and a fungicidally effective amount of a compound of the formula defined in claim 24.

34. A fungicidal composition comprising a biologically inert carrier and a fungicidally effective amount of a compound of the formula defined in claim 27.

35. A fungicidal composition comprising a biologically inert carrier and a fungicidally effective amount of a compound of the formula defined in claim 3.

36. A method for controlling fungi comprising contacting said fungi or their growth environment with a fungicidally effective amount of a compound of the formula defined in claim 1.

37. A method for controlling fungi comprising contacting said fungi or their growth environment with a fungicidally effective amount of a compound of the formula defined in claim 5.

38. A method for controlling fungi comprising contacting said fungi or their growth environment with a fungicidally effective amount of a compound of the formula defined in claim 9.

39. A method for controlling fungi comprising contacting said fungi or their growth environment with a fungicidally effective amount of a compound of the formula defined in claim 2.

40. A method for controlling fungi comprising contacting said fungi or their growth environment with a fungicidally effective amount of a compound of the formula defined in claim 21.

41. A method for controlling fungi comprising contacting said fungi or their growth environment with a fungicidally effective amount of a compound of the formula defined in claim 24.

42. A method for controlling fungi comprising contacting said fungi or their growth environment with a fungicidally effective amount of a compound of the formula defined in claim 27.

43. A method for controlling fungi comprising contacting said fungi or their growth environment with a fungicidally effective amount of a compound of the formula defined in claim 3.

* * * * *